(12) United States Patent
D'Angio et al.

(10) Patent No.: US 9,006,267 B2
(45) Date of Patent: *Apr. 14, 2015

(54) PHARMACEUTICAL COMPOSITIONS AND DOSAGE FORMS OF THALIDOMIDE

(75) Inventors: Paul D'Angio, Basking Ridge, NJ (US); John McCarty, Miami Springs, FL (US)

(73) Assignee: Celgene Corporation, Summit, NJ (US)

( * ) Notice: Subject to any disclaimer, the term of this patent is extended or adjusted under 35 U.S.C. 154(b) by 2377 days.

This patent is subject to a terminal disclaimer.

(21) Appl. No.: 11/384,381

(22) Filed: Mar. 21, 2006

(65) Prior Publication Data

US 2006/0216344 A1 Sep. 28, 2006

Related U.S. Application Data

(63) Continuation-in-part of application No. 10/608,077, filed on Jun. 30, 2003, now Pat. No. 7,230,012.

(60) Provisional application No. 60/426,016, filed on Nov. 14, 2002.

(51) Int. Cl.
*A61K 31/454* (2006.01)
*A61K 9/48* (2006.01)
*A61K 9/20* (2006.01)

(52) U.S. Cl.
CPC .............. *A61K 9/2054* (2013.01); *A61K 9/2031* (2013.01); *A61K 9/4858* (2013.01); *A61K 9/4866* (2013.01)

(58) Field of Classification Search
USPC .......................................... 424/451; 514/323
See application file for complete search history.

(56) References Cited

U.S. PATENT DOCUMENTS

| | | | | |
|---|---|---|---|---|
| 5,385,901 | A | 1/1995 | Kaplan et al. | 514/231.5 |
| 5,405,855 | A | 4/1995 | Andrulis, Jr. et al. | 514/323 |
| 5,434,170 | A | 7/1995 | Andrulis, Jr. et al. | 514/323 |
| 5,593,990 | A | 1/1997 | D'Amato | 514/235.2 |
| 5,629,327 | A | 5/1997 | D'Amato | 514/323 |
| 5,643,915 | A | 7/1997 | Andrulis, Jr. et al. | 514/279 |
| 5,654,312 | A | 8/1997 | Andrulis, Jr. et al. | 514/279 |
| 5,712,291 | A | 1/1998 | D'Amato | 514/323 |
| 5,731,325 | A | 3/1998 | Andrulis, Jr. et al. | 514/323 |
| 6,001,828 | A | 12/1999 | Andrulis, Jr. et al. | 514/221 |
| 6,071,948 | A | 6/2000 | D'Amato | 514/416 |
| 6,114,355 | A | 9/2000 | D'Amato | 514/323 |
| 6,140,346 | A | 10/2000 | Andrulis, Jr. et al. | 514/323 |
| 6,228,879 | B1 | 5/2001 | D'Amato | 514/416 |
| 6,235,756 | B1 | 5/2001 | D'Amato | 514/323 |
| 6,469,045 | B1 | 10/2002 | D'Amato | 514/416 |
| 6,914,067 | B2 | 7/2005 | Govindarajan et al. | |
| 2001/0018445 | A1 | 8/2001 | Huang et al. | |
| 2003/0191098 | A1 | 10/2003 | D'Amato | 514/171 |

FOREIGN PATENT DOCUMENTS

| WO | WO 01/74362 | 10/2001 |
|---|---|---|
| WO | WO 03/080048 | 10/2003 |

OTHER PUBLICATIONS

Gennaro, Remington: The Science and Practice of Pharmacy, Mack Publishing Co. 19th, 1615-1619, 1642-1649; especially 1618 and 1642-1644, (1995).*
Alebiowu et al., HighBeam Research, "Effects of natural and pregelatinized sorghum, plantain, and corn starch binders on the compressional characteristics of a paracetamol table formulation", http://www.highbeam.com/doc/1P3-82178662.html, pp. 1-4, Jan. 2001.*
Clark et al., "Thalidomid (Thalidomide) Capsules," *Drug Safety*, 24(2):87-117 (2001).
Scheffler et al. "Thalidomide does not alter estrogen-progesterone hormone single-dose pharmacokinetics," *Clin. Pharmacol. Ther.* 65:483-490 (1999).
Teo et al. "Effect of a high-fat meal on thalidomide pharmacokinetics and the relative bioavailability of oral formulations in healthy men and women," *Biopharmaceuticals and Drug Disposition*, 21:33-40 (2000).
Teo et al., "Lack of peripheral neuropathy in Beagle dogs after 53 weeks oral administration of thalidomide capsules," *Human and Experimental toxicology*, 19:615-622 (2000).
U.S. Appl. No. 10/608,077; (U.S. Patent No. 7,230,012) Office Action Dated Aug. 11, 2005.
U.S. Appl. No. 10/608,077; (U.S. Patent No. 7,230,012) Interview Summary Dated Dec. 15, 2005.
U.S. Appl. No. 10/608,077; (U.S. Patent No. 7,230,012) Office Action Dated Apr. 19, 2006.
U.S. Appl. No. 10/608,077; (U.S. Patent No. 7,230,012) Interview Summary Dated Jun. 6, 2006.
U.S. Appl. No. 10/608,077; (U.S. Patent No. 7,230,012) Office Action Dated Jun. 29, 2006.
U.S. Appl. No. 10/608,077; (U.S. Patent No. 7,230,012) Notice of Allowance Dated Apr. 10, 2007.
Notification Pursuant to § 505(j)(2)(B)(ii) of the Federal Food, Drug and Cosmetic Act by Barr Laboratories (2007).
Remington's Pharmaceutical Sciences, 18th Ed., Mack Publishing, Table of Contents and pp. 1658-1664 (1990).
Handbook of Pharmaceutical Excipients, 3rd Ed., American Pharmaceutical Association, USA and Pharmaceutical Press UK, Table of Contents and pp. 305-308 (2000).
"Thalidomide," Printout from www.grunenthal.com/cw/en_EN/html/cw_en_en_aboutus.jhtml?CatId=cw_en_en aboutus_e_01 (date unknown).
"Talizer," Printout from http://216.239.37.104/translate_c?hl=en &sl-es&u-http://www.facmed.unam.mx/bmnd/pl (date unknown).
"Sauramide," Printout from http://www.kodc.or.kr/jaga/suaramide_photo.htm (date unkown).

(Continued)

*Primary Examiner* — Lezah Roberts
(74) *Attorney, Agent, or Firm* — Jones Day

(57) ABSTRACT

Pharmaceutical compositions and single unit dosage forms of thalidomide and pharmaceutically acceptable stereoisomers, prodrugs, salts, solvates, hydrates, or clathrates are disclosed. Also disclosed are methods of treating, managing, and preventing diseases and conditions such as, but not limited to, leprosy, chronic graft-vs-host disease, rheumatoid arthritis, sarcoidosis, an inflammatory condition, inflammatory bowel disease, and cancer using the novel dosage forms disclosed herein.

12 Claims, No Drawings

(56) References Cited

OTHER PUBLICATIONS

"Notice Destinee Au Patient," Notice to Patients regarding Thalidomide Laphal (date unknown).

"Historical Timeline," Printout from http://www.pharmion.com/corporateweb/home.nsf/Content/HistoricalTimeline (date unknown).

"Thalidomide 100 mg Tablets (EntreMed Formulation)," Celgene internal document (date unknown).

"Products," Printout from http://www.daburpharma.com/htmls/prod_form.html (date unknown).

"Myrin (Thaidomide)," Printout from http://www.lipomed.com/Pharma/myrin/overview/ (date unknown).

"Thalomid," *Physician's Desk Reference*, 53th Ed., pp. 3457-3462 (1999).

"Thalomid," *Physician's Desk Reference*, 54th Ed., pp. 911-916 (2000).

"Thalomid," *Physician's Desk Reference*, 55th Ed., pp. 1081-1085 (2001).

"Thalomid," *Physician's Desk Reference*, 56th Ed., pp. 1154-1158 (2002).

"Thalomid," *Physician's Desk Reference*, 57th Ed., pp. 1153-1157 (2003).

"Thalomid," *Physician's Desk Reference*, 58th Ed., pp. 1122-1127 (2004).

"Thalomid," *Physician's Desk Reference*, 59th Ed., pp. 1095-1099 (2005).

"Getting Thalidomide," Printout from http://www.4imago.com/mpd/mexico.htm (May 12, 2004).

"Thalidomide," The Merck Index, $11^{th}$ Ed., p. 9182 (1989).

"Thalidomide," The Merck Index, $12^{th}$ Ed., p. 9389 (1996).

"Thalidomide," *The Merck Index*, $13^{th}$ Ed., p. 9323 (2001).

Guo et al., "A prototype intelligent hybrid system for hard gelatin capsule formulation development," *Pharmaceutical Technology*, pp. 44-60 (Sep. 2002).

Rouhi, "Thalidomide," Chemical & Engineering News, pp. 122-123 (Jun. 20, 2005).

"Thalidomide," *Drugs of the Future*, Entry # 91361 (2005).

Abdel-Razeq et al., *Drugs of the Future*, 29(10): 1059-1063 (2004).

Sommer, *Drugs of the Future*, 24(1): 67-75 (1999).

"Thalidomide," *Drug Data Report*, 17(5): 468 (1995).

"Thalidomide," *Drug Data Report*, 17(5): 482 (1995).

"Thalidomide," *Drug Data Report*, 20(11): 962 (1998).

\* cited by examiner ing Ser. No. 10/608,077, filed Jun. 30, 2003 now U.S. Pat.
PHARMACEUTICAL COMPOSITIONS AND DOSAGE FORMS OF THALIDOMIDE This application is a continuation-in-part of U.S. application Ser. No. 10/608,077, filed Jun. 30, 2003 now U.S. Pat. No. 7,230,012, which claims priority to provisional application No. 60/426,016, filed Nov. 14, 2002, both of which are incorporated herein by reference in their entireties.

1. FIELD OF THE INVENTION

The present invention relates, in part, to pharmaceutical compositions and dosage forms comprising thalidomide and pharmaceutically acceptable stereoisomers, prodrugs, salts, solvates, hydrates, and clathrates thereof. In particular, certain finished unit dosage forms comprising the active ingredient thalidomide and certain excipients in dosage strength of about 25, 50, 100, 150, or 200 mg are described herein. These are unique for their ease of manufacture and bioavailability characteristics.

2. BACKGROUND OF THE INVENTION

Thalidomide is a racemic compound sold under the trade name THALOMID® and chemically named α-(N-phthalimido)glutarimide or 2-(2,6-dioxo-3-piperidinyl)-1H-isoindole-1,3(2H)-dione. Thalidomide was originally developed to treat morning sickness, but it was withdrawn from use due to teratogenic effects. Thalidomide is currently approved in the United States for the treatment of erythema nodosum leprosum in humans. *Physician's Desk Reference®*, pp. 1081-1085 (55$^{th}$ Ed., 2001).

Thalidomide has reportedly been used on patients with leprosy, chronic graft-vs-host disease, rheumatoid arthritis, sarcoidosis, several inflammatory skin diseases, and inflammatory bowel disease. See generally, Koch, H. P., *Prog. Med. Chem.*, 22: 165-242 (1985). See also, Moller, D. R., et al., *J. Immunol.*, 159: 5157-5161 (1997); Vasiliauskas, E. A., et al., *Gastroenterology*, 117: 1278-1287 (1999); and Ehrenpreis, E. D., et al., *Gastroenterology*, 117: 1271-1277 (1999). It has further been alleged that thalidomide can be combined with other drugs to treat iscehemia/reperfusion associated with coronary and cerebral occlusion. U.S. Pat. No. 5,643,915.

More recently, thalidomide has been used in the treatment of specific types of cancers. These include refractory multiple myeloma, brain, melanoma, breast, colon, mesothelioma, and renal cell carcinoma. See, e.g., Singhal, S., et al., *New England J. Med.*, 341(21): 1565-1571 (1999); and Marx, G. M., et al., *Proc. Am. Soc. Clin. Oncology*, 18: 454a (1999). It has further been reported that thalidomide has been used to prevent the development of chronic cardiomyopathy in rats caused by doxorubicin. Costa, P. T., et al., *Blood*, 92(10: suppl. 1): 235b (1998). Other reports concerning the use of thalidomide in the treatment of specific cancers include combination with carboplatin in the treatment of glioblastoma multiforme. McCann, J., *Drug Topics*. pp. 41-42 (Jun. 21, 1999). Thalidomide has reportedly also been used as an antiemetic during the treatment of astrocytoma. Zwart, D., *Arzneim.-Forsch.*, 16(12): 1688-1689 (1966). A method of inhibiting of angiogenesis is disclosed by U.S. Pat. No. 6,235,756 B1, which is incorporated herein by reference.

Thalidomide is administered to patients orally. Prior to the present invention, thalidomide was orally administered in a size #0 capsule shell containing 12.5 percent weight by total weight of the composition. The capsule fill weight is 400 mg, so only 50 mg of thalidomide are included per capsule. For use in the treatment of diseases such as cancer, however, 200 mg to 800 mg dosages are commonly required. Therefore, patients had to ingest 4 to 16 capsules of thalidomide to receive a therapeutically effective amount of the drug when treating cancer. Because of the large size of the #0 capsule and the large amount of thalidomide required to treat certain diseases and conditions, patient compliance may be problematic. To be specific, some patients may not take thalidomide in its currently available oral dosage form as often or in the large amounts necessary to effectively treat their disease. Therefore, a need exists for new pharmaceutical dosage forms of thalidomide.

3. SUMMARY OF THE INVENTION

This invention encompasses novel pharmaceutical dosage forms of thalidomide and pharmaceutically acceptable stereoisomers, prodrugs, salts, solvates, hydrates, and clathrates thereof. The invention further encompasses methods of treating, managing, or preventing diseases and conditions such as, but not limited to, leprosy, chronic graft-vs-host disease, rheumatoid arthritis, sarcoidosis, an inflammatory condition, inflammatory bowel disease, and cancer, using thalidomide and pharmaceutically acceptable stereoisomers, prodrugs, salts, solvates, hydrates, and clathrates thereof in the novel dosage forms described herein.

3.1. Definitions

As used herein and unless otherwise indicated, a composition that is "substantially free" of a compound means that the composition contains less than about 20 percent by weight, more preferably less than about 10 percent by weight, even more preferably less than about 5 percent by weight, and most preferably less than about 3 percent by weight of the compound.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80 percent by weight of one stereoisomer of the compound and less than about 20 percent by weight of other stereoisomers of the compound, more preferably greater than about 90 percent by weight of one stereoisomer of the compound and less than about 10 percent by weight of the other stereoisomers of the compound, even more preferably greater than about 95 percent by weight of one stereoisomer of the compound and less than about 5 percent by weight of the other stereoisomers of the compound, and most preferably greater than about 97 percent by weight of one stereoisomer of the compound and less than about 3 percent by weight of the other stereoisomers of the compound.

As used herein and unless otherwise indicated, the term "enantiomerically pure" means a stereomerically pure composition of a compound having one chiral center.

As used herein, unless otherwise specified, the term "pharmaceutically acceptable salt(s)," as used herein includes, but is not limited to, salts of acidic or basic moieties of thalidomide. Basic moieties are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions. Suitable organic acids include, but are not limited to, maleic, fumaric, benzoic, ascorbic, succinic, acetic, formic, oxalic, propionic, tartaric, salicylic, citric, gluconic, lactic, mandelic, cinnamic, oleic, tannic, aspartic, stearic, palmitic, glycolic, glutamic, gluconic, glucaronic, saccharic, isonicotinic, methanesulfonic, ethanesulfonic, p-toluenesulfonic, benzenesulfonic acids, or pamoic (i.e., 1,1'-methylene-bis-(2-hydroxy-3-naphthoate) acids. Suitable inorganic acids include, but are not limited to, hydrochloric, hydrobromic, hydroiodic, sulfuric, phosphoric, or nitric acids. Compounds that include an amine moiety can form pharmaceutically acceptable salts with various amino acids, in addition to the acids mentioned above. Chemical moieties that are acidic in nature are capable of forming base salts with various pharmacologically acceptable cations. Examples of such salts are alkali metal or alkaline earth metal salts and, particularly, calcium, magnesium, sodium, lithium, zinc, potassium, or iron salts.

As used herein to describe a compound or chemical moiety, the term "derivative" means a compound or chemical moiety wherein the degree of saturation of at least one bond has been changed (e.g., a single bond has been changed to a double or triple bond) or wherein at least one hydrogen atom is replaced with a different atom or a chemical moiety. Examples of different atoms and chemical moieties include, but are not limited to, halogen, oxygen, nitrogen, sulfur, hydroxy, methoxy, alkyl, amine, amide, ketone, and aldehyde.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of thalidomide that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of thalidomide that include —NO, —NO$_2$, —ONO, or —ONO$_2$ moieties.

As used herein and unless otherwise indicated, the terms "biohydrolyzable carbamate," "biohydrolyzable carbonate," "biohydrolyzable ureide," "biohydrolyzable phosphate" mean a carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein and unless otherwise indicated, the term "biohydrolyzable ester" means an ester of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters.

As used herein and unless otherwise indicated, the term "biohydrolyzable amide" means an amide of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable amides include, but are not limited to, lower alkyl amides, α-amino acid amides, alkoxyacyl amides, and alkylaminoalkylcarbonyl amides.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder.

As used herein, and unless otherwise specified, the terms "prevent," "preventing" and "prevention" refer to the prevention of the onset, recurrence or spread of a disease or disorder, or of one or more symptoms thereof.

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic or therapeutic agent do not result in a cure of the disease or disorder.

As used herein, and unless otherwise specified, the term "about," when used in connection with doses, amounts, or weight percent of ingredients of a composition or a dosage form, means dose, amount, or weight percent that is recognized by those of ordinary skill in the art to provide a pharmacological effect equivalent to that obtained from the specified dose, amount, or weight percent is encompassed. Specifically, the term "about" contemplates a dose, amount, or weight percent within 15%, more specifically within 10%, more specifically within 5%, of the specified dose, amount, or weight percent is encompassed.

4. DETAILED DESCRIPTION OF THE INVENTION

This invention encompasses novel pharmaceutical dosage forms of thalidomide and pharmaceutically acceptable stereoisomers, prodrugs, salts, solvates, hydrates, and clathrates thereof. Preferred dosage forms are suitable for oral administration to a patient. Preferred oral dosage forms of thalidomide comprise a higher weight percent of thalidomide than prior oral dosage forms of the drug. Preferred oral dosage forms of thalidomide are either bioequivalent to the oral dosage forms of the drug currently approved by the Food and Drug Administration in the United States, or provide better bioavailability than currently approved dosage forms.

The invention also encompasses kits comprising pharmaceutical compositions and dosage forms of the invention. Also encompassed by the invention are methods of treating, managing, and preventing diseases and conditions which include administering to patients in need thereof pharmaceutical compositions and dosage forms of the invention.

For example, this invention encompasses a single unit dosage form suitable for oral administration to a human comprising: an amount equal to or greater than about 1, 5, 10, 15, 20, 25, 30, 50, 75, 100, 150, or 200 mg of an active ingredient; and an excipient; wherein the active ingredient is thalidomide or a pharmaceutically acceptable stereoisomer, prodrug, salt, solvate, or clathrate thereof. Preferably, the amount of active ingredient is from about 5 to about 10 weight percent when the active ingredient is about 1 to about 5 mgs. In one embodiment, the active ingredient is thalidomide.

A particular embodiment of the invention encompasses a single unit dosage form suitable for oral administration to a human comprising: an amount equal to or greater than about 25 mg of an active ingredient; and an excipient; wherein the active ingredient is thalidomide or a pharmaceutically acceptable stereoisomer, prodrug, salt, solvate, or clathrate thereof. Preferably, the amount of active ingredient is from about 10 to about 50 weight percent, more preferably about 20-40 weight percent when the active ingredient is about 25 mg or more.

In one embodiment, this invention comprises a single unit dosage form suitable for oral administration to a human comprising: an amount equal to about 20, 25, or 30 mg of an active ingredient, wherein the active ingredient is thalidomide or a pharmaceutically acceptable stereoisomer, prodrug, salt, solvate, or clathrate thereof; and about 90, 100, or 110 mg of a carrier, diluent or filler. In a specific embodiment, the amount of a carrier, diluent or filler is 99, more specifically, 99.4 mg. In one specific embodiment, the active ingredient and carrier, diluent, or filler are directly blended as described herein elsewhere. In another specific embodiment, the carrier, diluent or filler comprises pregelatinized corn starch, microcrystalline cellulose, silicified microcrystalline cellulose, and/or dicalcium phosphate. In another specific embodiment, the dosage form comprises magnesium stearate in an amount of about 0.5, 0.6, 0.7, 0.9, or 1 mg. In a specific embodiment, the amount of magnesium stearate is 0.63 mg. In another specific embodiment, the dosage form weighs about 125 mg. The dosage form may be in any form suitable for oral administration, including, but not limited to, a capsule or a tablet. In another specific embodiment, the single unit dosage form is in a capsule of size #4.

In one embodiment, this invention comprises a single unit dosage form suitable for oral administration to a human comprising: an amount equal to about 45, 50, or 55 mg of an active ingredient, wherein the active ingredient is thalidomide or a pharmaceutically acceptable stereoisomer, prodrug, salt, solvate, or clathrate thereof; and about 65, 70, 75, or 80 mg of a carrier, diluent or filler. In a specific embodiment, the amount of a carrier, diluent or filler is about 74, more specifically 74.4 mg. In one specific embodiment, the active ingredient and carrier, diluent, or filler are directly blended. In another specific embodiment, the carrier, diluent or filler comprises pregelatinized corn starch, microcrystalline cellulose, silicified microcrystalline cellulose, and/or dicalcium phosphate. In another specific embodiment, the dosage form comprises magnesium stearate in an amount of about 0.5, 0.6, 0.7, 0.9, or 1 mg. In a specific embodiment, the amount of magnesium stearate is 0.63 mg. In another specific embodiment, the dosage form weighs about 125 mg. The dosage form may be in any form suitable for oral administration, including, but not limited to, a capsule or a tablet. In another specific embodiment, the single unit dosage form is in a capsule of size #4.

In one embodiment, this invention encompasses a single unit dosage form suitable for oral administration to a human comprising: an amount equal to about 90, 100, or 110 mg of an active ingredient, wherein the active ingredient is thalidomide or a pharmaceutically acceptable stereoisomer, prodrug, salt, solvate, or clathrate thereof; and about 145, 150, or 155 mg of a carrier, diluent or filler. In one specific embodiment, the active ingredient and carrier, diluent, or filler are directly blended. In another specific embodiment, the carrier, diluent or filler comprises pregelatinized corn starch, microcrystalline cellulose, silicified microcrystalline cellulose, or dicalcium phosphate. In another specific embodiment, the dosage form comprises magnesium stearate in an amount of about 1, 1.25, 1.5, 1.75, or 2 mg. In another specific embodiment, the dosage form weighs about 250 mg. The dosage form may be in any form suitable for oral administration, including, but not limited to, a capsule or a tablet. In another specific embodiment, the single unit dosage form is in a capsule of size #2.

In one embodiment, this invention encompasses a single unit dosage form suitable for oral administration to a human comprising: an amount equal to about 130, 150, or 170 mg of an active ingredient, wherein the active ingredient is thalidomide or a pharmaceutically acceptable stereoisomer, prodrug, salt, solvate, or clathrate thereof; and about 200, 220, or 240 mg of a carrier, diluent or filler. In a specific embodiment, the amount of a carrier, diluent, or filler is 223, more specifically 223.1 mg. In one specific embodiment, the active ingredient and carrier, diluent, or filler are directly blended. In another specific embodiment, the carrier, diluent or filler comprises pregelatinized corn starch, microcrystalline cellulose, silicified microcrystalline cellulose, or dicalcium phosphate. In another specific embodiment, the dosage form comprises magnesium stearate in an amount of about 1, 1.5, 1.75, 2, or 2.5 mg. In a specific embodiment, the amount of magnesium stearate is 1.9, more specifically 1.88 mg. In another specific embodiment, the dosage form weighs about 375 mg. The dosage form may be in any form suitable for oral administration, including, but not limited to, a capsule or a tablet. In another specific embodiment, the single unit dosage form is in a capsule of size #1.

In one embodiment, this invention comprises a single unit dosage form suitable for oral administration to a human comprising: an amount equal to about 180, 200, or 220 mg of an active ingredient, wherein the active ingredient is thalidomide or a pharmaceutically acceptable stereoisomer, prodrug, salt, solvate, or clathrate thereof; about 270, 295, or 310 mg of a carrier, diluent or filler. In one specific embodiment, the amount of carrier, diluent, or filler is about 297, more specifically, about 297.5 mg. In another embodiment, the active ingredient and carrier, diluent, or filler are directly blended. In another specific embodiment, the carrier, diluent or filler comprises pregelatinized corn starch, microcrystalline cellulose, silicified microcrystalline cellulose, and/or dicalcium phosphate. In another specific embodiment, the dosage form comprises magnesium stearate in an amount of about 2, 2.5, 3, or 3.5 mg. In another specific embodiment, the dosage form weighs about 500 mg. The dosage form may be in any form suitable for oral administration, including, but not limited to, a capsule or a tablet. In another specific embodiment, the single unit dosage form is in a capsule of size #0.

Another specific example encompasses a single unit dosage form suitable for oral administration to a human comprising: about 40 weight percent of an active ingredient, wherein the active ingredient is thalidomide or a pharmaceutically acceptable stereoisomer, prodrug, salt, solvate, or clathrate thereof; about 53 weight percent of a binder, wherein the binder comprises pregelatinized corn starch or microcrystalline cellulose; about 4 weight percent surfactant; about 2 weight percent disintegrant; and about 1 weight percent lubricant. The dosage form may be in any form suitable for oral administration, including, but not limited to, a capsule or a tablet.

Another specific example encompasses a single unit dosage form suitable for oral administration to a human comprising: about 20 weight percent of an active ingredient, wherein the active ingredient is thalidomide or a pharmaceutically acceptable stereoisomer, prodrug, salt, solvate, or clathrate thereof; about 73 weight percent of a binder, wherein the binder comprises pregelatinized corn starch or microcrystalline cellulose; about 4 weight percent surfactant; about 2 weight percent disintegrant; and about 1 weight percent lubricant. The dosage form may be in any form suitable for oral administration, including, but not limited to, a capsule or a tablet.

Another embodiment of the invention encompasses a method for treating, managing, or preventing leprosy, chronic graft-vs-host disease, rheumatoid arthritis, sarcoidosis, an inflammatory condition, inflammatory bowel disease, or cancer, which comprises administering to a patient in need of such treatment or prevention a single unit dosage form of the invention as described herein. In a preferred method, the disease is cancer.

This invention encompasses pharmaceutical compositions and single unit dosage forms of racemic and stereomerically pure thalidomide, and pharmaceutically acceptable stereoisomers, prodrugs, salts, solvates, hydrates, and clathrates thereof.

Thalidomide is commercially available, but can also be prepared by methods known in the art. See, e.g., *The Merck Index*, p. 9182 (11$^{th}$ ed.; 1989), and the references disclosed therein.

4.1. Pharmaceutical Compositions and Dosage Forms

Pharmaceutical compositions and dosage forms of the invention contain a prophylactically or therapeutically effective amount of an active ingredient (i.e., thalidomide or a pharmaceutically acceptable stereoisomer, prodrug, salt, solvate, hydrate, or clathrate thereof) and an excipient. Preferred dosage forms are suitable for oral administration, and can be coated to reduce or avoid degradation of the active ingredient within the gastrointestinal tract.

Pharmaceutical compositions and dosage forms of the invention may also contain one or more secondary active ingredients. Examples of secondary active ingredients include, but are not limited to, anti-cancer drugs. Examples of anti-cancer drugs include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Preferred pharmaceutical compositions and dosage forms contain greater than about 10, 15, 20, 25, 30, 35, 40, 45, 50, 55, or 60 weight percent active ingredient (i.e., thalidomide or a pharmaceutically acceptable stereoisomer, prodrug, salt, solvate, hydrate, or clathrate thereof). Pharmaceutical compositions and dosage forms encompassed by the invention typically contain the active ingredient in an amount of from about 10 percent to about 60 percent by weight, specifically from about 20 percent to about 50 percent by weight, and more specifically about 20 percent to about 40 percent by weight of the total composition or dosage form.

Pharmaceutical compositions and dosage forms of the invention may contain one or more excipients in an amount of less than about 90, 85, 80, 75, 70, 65, 60, 55, 50, 45, or 40 percent by weight of the total composition or dosage form. Pharmaceutical compositions and dosage forms encompassed by the invention typically contain the excipient(s) in an amount of from about 50 percent to about 90 percent by weight, preferably from about 60 percent to about 80 percent by weight, more preferably in an amount of from about 60 percent to about 75 percent by weight.

Excipients include, but are not limited to, carriers, diluents, fillers, lubricants and glidants. See Rowe et al., *Handbook of Pharmaceutical Excipients*, 4$^{th}$ Ed. (2003), which is incorporated herein by reference. One embodiment of the invention encompasses a pharmaceutical composition that includes thalidomide, and a carrier, diluent or filler. The carrier, diluent or filler is preferably present in an amount from about 40 percent to about 85 percent by weight, preferably from about 55 percent to about 75 percent by weight. A preferred pharmaceutical composition further includes a lubricant or glidant in an amount of from about 0.01 percent to about 4 percent by weight, and more specifically in an amount from about 0.1 percent to about 1 percent. In yet another embodiment, the composition further includes a disintegrant, specifically, in an amount from about 1 percent to about 8 weight percent, more specifically from about 1 percent to about 3 weight percent.

Carriers, diluents and fillers are used to give the powder (e.g., in the tablet or capsule) bulk so that an acceptable size tablet, capsule or other desirable dosage form is produced. Typically, therapeutic ingredients are formed in a convenient dosage form of suitable size by the incorporation of a diluent therewith. In some instances, binding of the drug(s) to the filler may occur and affect bioavailability. Consequently, a sufficient amount of filler should be used to achieve a desired dilution ratio without detrimentally affecting release of the drug ingredients from the dosage form containing the filler. Further, a filler that is physically and chemically compatible with the therapeutic ingredient(s) of the dosage form should be used. The amount of filler used varies upon the type of formulation and mode of administration. Carriers, diluents, or fillers suitable for use in pharmaceutical compositions and dosage forms include, but are not limited to, calcium carbonate (e.g., granules or powder), calcium phosphate, dibasic calcium phosphate, tribasic calcium sulfate, calcium carboxymethylcellulose, cellulose (e.g., microcrystalline cellulose, silicified microcrystalline cellulose, and cellulose acetate), dextrates, dextrin, dextrose (glucose), fructose, kaolin, lactitol, lactose, magnesium carbonate, magnesium oxide, mannitol, maltodextrins, maltose, silicic acid, sorbitol, starch (e.g., pregelatinized starch), sucrose, sugar, talc, xylitol, and mixtures thereof.

One example of a pre-gelatinized starch is SPRESS B-820. Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), PROSOLV SMCC 90HD (Penwest, Patterson, N.Y.), and mixtures thereof. Carriers, diluents and fillers may also be used in premixes.

Lubricants are used to enhance the flow of the powder mix to the manufacturing machine and to prevent sticking of the dosage form after it is manufactured. Too little lubricant will not permit satisfactory manufacturing characteristics and too much may produce a dosage form with a water-impervious hydrophobic coating, which can form because lubricants are usually hydrophobic materials such as stearic acid, magnesium stearate, calcium stearate and the like. Further, a water-impervious hydrophobic coating can inhibit disintegration of the dosage form and dissolution of the drug ingredient(s). Thus, a sufficient amount of lubricant should be used that readily allows release of the active ingredient(s) without forming a water-impervious hydrophobic coating that detrimentally interferes with the desired disintegration and/or dissolution of the drug ingredient(s). Lubricants that can be used in pharmaceutical compositions and dosage forms of the invention include, but are not limited to, agar, calcium stearate, ethyl oleate, ethyl laureate, glycerin, glyceryl palmitostearate, mineral oil, hydrogenated vegetable oil (e.g., corn oil, cottonseed oil, olive oil, peanut oil, sesame oil, soybean oil, and sunflower oil), magnesium oxide, magnesium stearate, mannitol, poloxamer, glycols (e.g., polyethylene glycol), sodium benzoate, sodium lauryl sulfate, sodium stearyl, sorbitol, stearic acid, talc, zinc stearate, and mixtures thereof.

Glidants include, for example, coagulated aerosols of synthetic silica colliodal silicon dioxide, magnesium trisilicate, powdered cellulose, pyrogenic silicon dioxide products (e.g., CAB-O-SIL sold by Cabot Co. of Boston, Mass.), starch, syloid silica gels (e.g., AEROSIL 200, manufactured by W.R. Grace Co. of Baltimore, Md.), talc, tribasic calcium phosphate, and mixtures thereof. If used, lubricants are typically used in an amount of less than about 1 weight percent of the pharmaceutical compositions or dosage forms into which they are incorporated.

Disintegrants are used in the compositions of the invention to provide dosage forms that disintegrate when exposed to an aqueous environment. Dosage forms that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form the compositions of the invention. The amount of disintegrant used varies based upon the type of formulation, and is readily discernible to those of ordinary skill in the art. Disintegrants that can be used in pharmaceutical compositions and dosage forms of the invention include, but are not limited to, agar-agar, algins (e.g., alginic acid), calcium carbonate, carboxmethylcellulose, cellulose (e.g., hydroxypropyl cellulose, microcrystalline cellulose, and silicified microcrystalline cellulose), clays, colloid silicon dioxide, croscarmellose sodium, crospovidone, gums, magnesuim aluminium silicate, methylcellulose, microcrystalline cellulose, polacrilin potassium, pre-gelatinized starch, sodium alginate, sodium starch glycolate, starch (e.g., pregelatinized starch, potato starch, and tapioca starch), and mixtures thereof.

Pharmaceutical compositions and dosage forms can also contain other excipients. Surfactants are used in dosage forms to improve the wetting characteristics and/or to enhance dissolution, and are particularly useful in pharmaceutical compositions or dosage forms containing poorly soluble or insoluble drug(s) or active ingredients. Examples of surfactants include, but are not limited to, polyoxyethylene sorbitan fatty acid esters, such as those commercially available as TWEENs (e.g. Tween 20 and Tween 80), polyethylene glycols, polyoxyethylene stearates, polyvinyl alcohol, polyvinylpyrrolidone, poly(oxyethylene)/poly(oxypropylene) block co-polymers such as poloxamers (e.g., commercially available as PLURONICs), and tetrafunctional block copolymers derived from sequential addition of propylene oxide and ethylene oxide to ethylenediamine, such as polyxamines (e.g., commercially as TETRONICs (BASF)), dextran, lecithin, dialkylesters of sodium sulfosuccinic acid, such as Aerosol OT, sodium lauryl sulfate, alkyl aryl polyether sulfonates or alcohols, such as TRITON X-200 or tyloxapol, p-isononylphenoxypoly (glycidol) (e.g. Olin-10G or Surfactant 10-G (Olin Chemicals), or mixtures thereof. Other pharmaceutically acceptable surfactants are well known in the art, and are described in detail in the *Handbook of Pharmaceutical Excipients*, $4^{th}$ Ed., Pharmaceutical Press, London, UK and American Pharmaceutical Association, Washington, D.C. (2003).

Other classes of additives for use with the pharmaceutical compositions or dosage forms of the present invention include, but are not limited to, anti-caking or antiadherent agents, antimicrobial preservatives, coating agents, colorants, desiccants, flavors and perfumes, plasticizers, viscosity increasing agents, sweeteners, buffering agents, humectants and the like.

Examples of anti-caking agents include, but are not limited to, calcium silicate, magnesium silicate, silicon dioxide, colloidal silicon dioxide, talc, and mixtures thereof.

Examples of antimicrobial preservatives include, but are not limited to, benzalkonium chloride solution, benzethonium chloride, benzoic acid, benzyl alcohol, butyl paraben, cetylpyridinium chloride, chlorobutanol, cresol, dehydroacetic acid, ethylparaben, methylparaben, phenol, phenylethyl alcohol, phenylmercuric acetate, phenylmercuric nitrate, potassium sorbate, propylparaben, sodium benzoate, sodium dehydroacetate, sodium propionate, sorbic acid, thimersol, thymol, and mixtures thereof.

Examples of colorants for use with the present invention include, but are not limited to, pharmaceutically acceptable dyes and lakes, caramel, red ferric oxide, yellow ferric oxide or mixtures thereof. Examples of desiccants include, but are not limited to, calcium chloride, calcium sulfate, silica gel and mixtures thereof.

Flavors that may be used include, but are not limited to, acacia, tragacanth, almond oil, anethole, anise oil, benzaldehyde, caraway, caraway oil, cardamom oil, cardamom seed, compound cardamom tincture, cherry juice, cinnamon, cinnamon oil, clove oil, cocoa, coriander oil, eriodictyon, eriodictyon fluidextract, ethyl acetate, ethyl vanillin, eucalyptus oil, fennel oil, glycyrrhiza, pure glycyrrhiza extract, glycyrrhiza fluidextract, lavender oil, lemon oil, menthol, methyl salicylate, monosodium glutamate, nutmeg oil, orange flower oil, orange flower water, orange oil, sweet orange peel tincture, compound orange spirit, peppermint, peppermint oil, peppermint spirit, pine needle oil, rose oil, stronger rose water, spearmint, spearmint oil, thymol, tolu balsam tincture, vanilla, vanilla tincture, and vanillin and mixture thereof.

Examples of sweetening agents include, but are not limited to, aspartame, dextrates, mannitol, saccharin, saccharin calcium, saccharin sodium, sorbitol, sorbitol solution, and mixtures thereof.

Exemplary plasticizers for use with the present invention include, but are not limited to, castor oil, diacetylated monoglycerides, diethyl phthalate, glycerin, mono- and diacetylated monoglycerides, polyethylene glycol, propylene glycol, and triacetin or mixtures thereof. Suitable viscosity increasing agents include, but are not limited to, acacia, agar, alamic acid, aluminum monostearate, bentonite, bentonite magma, carbomer 934, carboxymethylcellulose calcium, carboxymethylcellulose sodium, carboxymethylcellulose sodium 12, carrageenan, cellulose, microcrystalline cellulose, gelatin, guar gum, hydroxyethyl cellulose, hydroxypropyl cellulose, hydroxypropyl methylcellulose (Nos. 2208; 2906; 2910), magnesium aluminum silicate, methylcellulose, pectin, polyvinyl alcohol, povidone, silica gel, colloidal silicon dioxide, sodium alginate, tragacanth and xanthan gum and mixtures thereof.

Buffering agents that may be used in the present invention include, but are not limited to, magnesium hydroxide, aluminum hydroxide and the like, or mixtures thereof. Examples of humectants include, but are not limited to, glycerol, other humectants and mixtures thereof.

Pharmaceutical compositions of the invention suitable for administration can be presented as discrete dosage forms, such as capsules (e.g., gelcaps), caplets, tablets, troches, lozenges, dispersions, and suppositories each containing a predetermined amount of an active ingredient as a powder or in granules, a solution, or a suspension in an aqueous or non-aqueous liquid, an oil-in-water emulsion, or a water-in-oil liquid emulsion. Because of their ease of administration, tablets, caplets, and capsules represent a preferred oral dosage unit forms.

Preferred tablets, caplets, and capsules contain from about 50 mg to about 500 mg of the pharmaceutical composition (i.e., active ingredient and excipient(s)), more preferably from about 125 mg to about 500 mg of the composition. Specific single unit dosage forms of the invention contain 25, 50, 100, 150, 200, 250, 300, 350, 400, 450, 500, 750, or 1000 mg of active ingredient. Capsules can be of any size. Examples of standard sizes include #000, #00, #0, #1, #2, #3, #4, and #5. See, e.g., *Remington's Pharmaceutical Sciences*, page 1658-1659 (Alfonso Gennaro ed., Mack Publishing Company, Easton Pa., 18th ed., 1990), which is incorporated by reference. Preferred capsules of the invention are of size #0, #1, #2, or #4.

A specific embodiment of the invention encompasses a single unit dosage form weighing about 125 mg, of which about 25 mg is active ingredient. Another embodiment weighs about 125 mg, of which about 50 mg is active ingredient. In these embodiments, the composition is preferably loaded into a size #4 capsule. Another embodiment weighs about 250 mg, of which about 100 mg is active ingredient. In this embodiment, the composition is preferably loaded into a size #2 capsule. Another embodiment weighs about 375 mg, of which about 150 mg is active ingredient. In this embodiment, the composition is preferably loaded into a size #1 capsule. Yet another single unit dosage form weighs about 500 mg and contains about 200 mg active ingredient. In this embodiment, the composition is preferably loaded into a size #0 capsule.

Table 1 illustrates examples of oral dosage forms of thalidomide encompassed by the present invention:

TABLE 1

Encapsulated Thalidomide Dosages

| Capsule Size | Composition Weight (mg) | Active Ingredient Dose (mg) |
|---|---|---|
| #0 | 500 | 200 |
| #1 | 375 | 150 |
| #2 | 250 | 100 |
| #4 | 125 | 50 |
| #4 | 125 | 25 |

Also encompassed by this invention are anhydrous pharmaceutical compositions and dosage forms including an active ingredient, since water can facilitate the degradation of some compounds. For example, the addition of water (e.g., 5 percent) is widely accepted in the pharmaceutical arts as a means of simulating shelf-life, i.e., long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate decomposition. Thus, the effect of water on a formulation can be of great significance since moisture and/or humidity are commonly encountered during manufacture, handling, packaging, storage, shipment, and use of formulations.

An anhydrous pharmaceutical composition should be prepared and stored such that the anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastic or the like, unit dose containers, blister packs, and strip packs.

In this regard, the invention encompasses a method of preparing a solid pharmaceutical formulation including an active ingredient through admixing the active ingredient and an excipient under anhydrous or low moisture/humidity conditions, wherein the ingredients are substantially free of water. The method can further include packaging the anhydrous or non-hygroscopic solid formulation under low moisture conditions. By using such conditions, the risk of contact with water is reduced and the degradation of the active ingredient can be prevented or substantially reduced.

This invention further encompasses lactose-free pharmaceutical compositions and dosage forms. Compositions and dosage forms that comprise an active ingredient that is a primary or secondary amine are preferably lactose-free. As used herein, the term "lactose-free" means that the amount of lactose present, if any, is insufficient to substantially increase the degradation rate of an active ingredient that is a primary or secondary amine.

Lactose-free compositions of the invention can comprise excipients which are well known in the art and are listed in the USP (XXI)/NF (XVI), which is incorporated herein by reference. In general, lactose-free compositions comprise an active ingredient, a binder/filler, and a lubricant in pharmaceutically compatible and pharmaceutically acceptable amounts. Preferred lactose-free dosage forms comprise an active ingredient, microcrystalline cellulose, pre-gelatinized starch, and magnesium stearate.

4.2. Process for Making Dosage Forms

Dosage forms of the present invention can be prepared by any of the methods of pharmacy, but all methods include the step of bringing the active ingredient into association with the excipient, which constitutes one or more necessary ingredients. In general, the compositions are prepared by uniformly admixing (e.g., direct blend) the active ingredient with liquid excipients or finely divided solid excipients or both, and then, if necessary, shaping the product into the desired presentation (e.g., compaction such as roller-compaction). If desired, tablets can be coated by standard aqueous or nonaqueous techniques.

A dosage form of the invention can be prepared by compression or molding, optionally with one or more accessory ingredients. Compressed tablets can be prepared by compressing in a suitable machine the active ingredient in a free-flowing form such as powder or granules, optionally mixed with an excipient as above and/or a surface active or dispersing agent. Molded tablets can be made by molding in a suitable machine a mixture of the powdered compound moistened with an inert liquid diluent. Encapsulation of the dosage forms of the invention can be done using capsules of methylcellulose, calcium alginate, or gelatin.

In some embodiments, the active ingredients and excipients are directly blended and loaded into, for example, a capsule, or compressed directly into tablets. A direct-blended dosage form may be more advantageous than a compacted (e.g., roller-compacted) dosage form in certain instances, since direct-blending can reduce or eliminate the harmful health effects that may be caused by airborne particles of ingredients (e.g., thalidomide, which is of potential health concern) during the manufacture using compaction process.

Direct blend formulations may be advantageous in certain instances because they require only one blending step, that of the active and excipients, before being processed into the final dosage form, e.g., tablet or capsule. This can reduce the production of airborne particle or dust to a minimum, while roller-compaction processes may be prone to produce dust. In roller-compaction process, the compacted material is often milled into smaller particles for further processing. The milling operation can produce significant amounts of airborne particles, since the purpose for this step in manufacturing is to reduce the materials particle size. The milled material is then blended with other ingredients prior to manufacturing the final dosage form.

For certain active ingredients, in particular for a compound with a low solubility such as thalidomide, the active ingredient's particle size is reduced to a fine powder in order to help increase the active ingredient's rate of solubilization. The increase in the rate of solubilization is often necessary for the active ingredient to be effectively absorbed in the gastrointestinal tract. However for fine powders to be directly-blended and loaded onto capsules, the excipients should preferably provide certain characteristics which render the ingredients suitable for the direct-blend process. Examples of such characteristics include, but are not limited to, acceptable flow characteristics. In one embodiment, therefore, this invention encompasses the use of, and compositions comprising, excipients which may provide characteristics, which render the resulting mixture suitable for direct-blend process, e.g., good flow characteristics.

4.2.1. Screening

The process for making the pharmaceutical compositions of the invention preferably includes the screening of the active ingredient and the excipient(s). Preferably, the active ingredient is passed through a screen having openings of about 430 microns to about 750 microns. More preferably, the active ingredient is passed through a screen with openings of about 600 microns to about 720 microns. In one embodiment, thalidomide is passed through a screen having openings of about 710 microns. Depending on the excipient(s) used, the screen openings vary. For example, disintegrants and binders are preferably passed through openings of about 430 microns to about 750 microns, more preferably from about 600 microns to about 720 microns, and most preferably about 710 microns. Lubricants are preferably passed through smaller openings, e.g., about 150 microns to about 250 microns screen. In one embodiment, the lubricant is passed through a screen opening of about 210 microns.

4.2.2. Pre-Blending

After the ingredients are screened, the excipient and active ingredient are preferably mixed in a diffusion mixer. In one embodiment, the mixing time is from about 1 minute to about 50 minutes, preferably from about 5 minutes to about 45 minutes. More preferably, the mixing time is from about 10 minutes to about 40 minutes, and most preferably the mixing time is from about 10 minutes to about 25 minutes. In another embodiment, the mixing time is about 15 minutes.

When more than one excipient is used, the excipients may be admixed in a tumble blender for about 1 minute to about 20 minutes, preferably for about 5 minutes to about 10 minutes, prior to mixing with the active ingredient.

4.2.3. Roller Compaction

In one embodiment, the pre-blend may optionally be passed through a roller compactor with a hammer mill attached at the discharge of the compactor.

4.2.4. Final Blend

When a lubricant, e.g., magnesium stearate, is used, the lubricant is mixed with the pre-blend at the end of the process to complete the pharmaceutical composition. This additional mixing is preferably from about 1 minute to about 10 minutes, more preferably about 3 minutes to about 5 minutes.

4.2.5. Encapsulation

The formulation mixture is then encapsulated into the desired size capsule shell using, for example, a capsule filling machine or a rotary tablet press.

4.3. Kits

Pharmaceutical packs or kits which comprise pharmaceutical compositions or dosage forms disclosed herein are also encompassed by the present invention. An example of a kit comprises notice in the form prescribed by a governmental agency regulating the manufacture, use or sale of pharmaceuticals or biological products, which notice reflects approval by the agency of manufacture, use or sale for human administration.

4.4. Methods of Treatment and Prevention

The present invention is also directed to methods of treating, managing, and preventing a wide variety diseases and conditions in patients (e.g., mammals, including humans). Examples of such disease and conditions include, but are not limited to, leprosy, chronic graft-vs-host disease, rheumatoid arthritis, sarcoidosis, inflammatory conditions (e.g., inflammation of the skin), inflammatory bowel disease, and cancer. Examples of cancers that can be treated using pharmaceutical compositions and dosage forms of the invention include, but are not limited to, primary and metastatic cancer of the head, neck, eye, mouth, throat, subcutaneous tissue, lymph nodes, esophagus, chest, bone, intestine, lung, colon, rectum, stomach, heart, prostate, breast, ovaries, adrenals, kidney, liver, pancreas, and brain. Specific examples of cancers that can be treated include, but are not limited to: AIDS associated leukemia and adult T-cell leukemia lymphoma; anal carcinoma; astrocytoma; biliary tract cancer; cancer of the bladder, including bladder carcinoma; brain cancer, including glioblastomas and medulloblastomas; breast cancer, including breast carcinoma; cervical cancer; choriocarcinoma; colon cancer including colorectal carcinoma; endometrial cancer; esophageal cancer; Ewing's sarcoma; gastric cancer; gestational trophoblastic carcinoma; glioma; hairy cell leukemia; head and neck carcinoma; hematological neoplasms, including acute and chronic lymphocytic and myelogeneous leukemia; hepatocellular carcinoma; Kaposi's sarcoma; kidney cancer; multiple myeloma; intraepithelial neoplasms, including Bowen's disease and Paget's disease; liver cancer; lung cancer including small cell carcinoma; lymphomas, including Hodgkin's disease, lymphocytic lymphomas, non-Hodgkin's lymphoma, Burkitt's lymphoma, diffuse large cell lymphoma, follicular mixed lymphoma, and lymphoblastic lymphoma; lymphocytic leukemia; neuroblastomas; oral cancer, including squamous cell carcinoma; ovarian cancer, including those arising from epithelial cells, stromal cells, germ cells and mesenchymal cells; pancreatic cancer; prostate cancer; rectal cancer; sarcomas, including soft tissue sarcomas, leiomyosarcoma, rhabdomyosarcoma, liposarcoma, fibrosarcoma, and osteosarcoma; skin cancer, including melanoma, Kaposi's sarcoma, basal cell cancer and squamous cell cancer; testicular cancer, including testicular carcinoma and germinal tumors (e.g., semicoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilm's tumor. The term "colorectal carcinoma" refers to disease of skin tissues, organs, bloods, and vessels, of the colon, sigmoid, and/or rectum and within the vicinity of the colon, sigmoid, and/or rectum.

Other diseases and conditions that can be treated using pharmaceutical compositions of this invention are disclosed in U.S. Pat. Nos. 5,712,291 and 6,235,756 to D'Amato, both of which are incorporated herein by reference.

The invention also encompasses a method of reducing or preventing an adverse effect associated with chemotherapy or radiation therapy, which comprises administering to a patient in need of such treatment or prevention a pharmaceutical composition or dosage form of the invention in an amount sufficient to reduce an adverse effect associated with the chemotherapy or radiation therapy. This embodiment includes the use of pharmaceutical compositions and dosage forms to protect against or treat an adverse effect associated with the use of chemotherapy or radiation therapy, including raising a patient's tolerance for chemotherapy or radiation therapy.

Examples of adverse effects associated with chemotherapy and radiation therapy include, but are not limited to: gastrointestinal toxicity such as, but not limited to, early and late-forming diarrhea and flatulence; nausea; vomiting; anorexia; leukopenia; anemia; neutropenia; asthenia; abdominal cramping; fever; pain; loss of body weight; dehydration; alopecia; dyspnea; insomnia; dizziness, mucositis, xerostomia, and kidney failure.

The actual amount of an active ingredient administered to a patient can depend on a variety of factors, such as, but not limited to, the disease or condition being treated or prevented, the specific active ingredient, and the method of its administration. For example, the dose and/or dose frequency may also vary according to age, body weight, response, and the past medical history of the patient. Suitable dosing regimens can be readily selected by those skilled in the art with due consideration of such factors by following, for example, dosages reported in the literature and recommended in the *Physician's Desk Reference®* (55th ed., 2001).

In one embodiment of the invention, an active ingredient is administered orally and daily in an amount of from about 50 to about 2000 mg, preferably from about 50 to about 1000 mg, and more preferably from about 50 to 800 mg. In a preferred embodiment, the recommended dose of active ingredient is from about 200 mg to about 800 mg.

5. EXAMPLES

Embodiments of the present invention may be more fully understood by reference to the following examples. While these examples are meant to be illustrative of pharmaceutical compositions and dosage forms made according to the present invention, the present invention is not meant to be limited by the following examples. All parts are by weight unless otherwise specified.

5.1. Example 1

25 mg Thalidomide Dosage Capsule

Table 2 illustrates a batch formulation and single dosage formulation for a 25 mg thalidomide single dose unit in a size #4 capsule.

TABLE 2

| Formulation for 25 mg thalidomide capsule | | | |
|---|---|---|---|
| Material | Percent By Weight | Quantity (mg/capsule) | Quantity (kg/batch) |
| Thalidomide | 20.0% | 25 mg | 5 kg |
| Pregelatinized Corn Starch, NF | 79.5% | 99.375 mg | 19.875 kg |
| Magnesium Stearate | 0.5% | 0.625 mg | 0.125 kg |
| Total | 100.0% | 125 mg | 25.00 kg |

The pregelatinized corn starch (SPRESS B-820) and thalidomide components were passed through a 710 μm screen and then loaded into a Diffusion Mixer with a baffle insert and blended for 20 minutes. The magnesium stearate was passed through a 250lm screen and added to the Diffusion Mixer. The mixture was blended for 3 minutes. The directly-blended final mixture was then encapsulated in a size #4 capsule, 125 mg per capsule (200,000 capsule batch size) using a Dosator type capsule filling machine.

5.2. Example 2

50 mg Thalidomide Dosage Capsule

Table 3 illustrates a batch formulation and single dosage formulation for a 50 mg thalidomide single dose unit in a size #4 capsule.

TABLE 3

| Formulation for 50 mg thalidomide capsule | | | |
|---|---|---|---|
| Material | Percent By Weight | Quantity (mg/capsule) | Quantity (kg/batch) |
| Thalidomide | 40.0% | 50 mg | 20 kg |
| Pregelatinized Corn Starch, NF | 59.5% | 74.375 mg | 29.75 kg |
| Magnesium Stearate | 0.5% | 0.625 mg | 0.25 kg |
| Total | 100.0% | 125 mg | 50 kg |

The pregelatinized corn starch (SPRESS B-820) and thalidomide components were passed through a 710 μm screen and then loaded into a V-blender and blended for 12 minutes. The magnesium stearate was passed through a 500 μm screen and added to the V-blender. The mixture was blended for 4 minutes. The directly-blended final mixture was then encapsulated in a size #4 capsule, 125 mg per capsule (400,000 capsule batch size) using a Dosator type capsule filling machine.

5.3. Example 3

100 mg Thalidomide Dosage Capsule

Table 4 illustrates a batch formulation and single dosage formulation for a 100 mg thalidomide single dose unit in a size #2 capsule.

TABLE 4

Formulation for 25 mg thalidomide capsule

| Material | Percent By Weight | Quantity (mg/capsule) | Quantity (kg/batch) |
|---|---|---|---|
| Thalidomide | 40.0% | 100 mg | 20 kg |
| Pregelatinized Corn Starch, NF | 59.5% | 148.75 mg | 29.75 kg |
| Magnesium Stearate | 0.5% | 1.25 mg | 0.25 kg |
| Total | 100.0% | 250 mg | 50.00 kg |

The pregelatinized corn starch (SPRESS B-820) and thalidomide components were passed through a 710 μm screen and then loaded into a V-blender and blended for 12 minutes. The magnesium stearate was passed through a 250 μm screen and added to the V-blender. The mixture was blended for 4 minutes. The directly-blended final mixture was then encapsulated in a size #2 capsule, 250 mg per capsule (200,000 capsule batch size) using a Dosator type capsule filling machine.

5.4. Example 4

150 mg Thalidomide Dosage Capsule

Table 5 illustrates a batch formulation and single dosage formulation for a 150 mg thalidomide single dose unit in a size #1 capsule.

TABLE 5

Formulation for 150 mg thalidomide capsule

| Material | Percent By Weight | Quantity (mg/capsule) | Quantity (kg/batch) |
|---|---|---|---|
| Thalidomide | 40.0% | 150 mg | 16.8 kg |
| Pregelatinized Corn Starch, NF | 59.5% | 223.125 mg | 24.99 kg |
| Magnesium Stearate | 0.5% | 1.875 mg | 0.21 kg |
| Total | 100.0% | 375 mg | 42.00 kg |

The pregelatinized corn starch (SPRESS B-820) and thalidomide components were passed through a 710 μm screen and then loaded into a drum blender and blended for 15 minutes. The magnesium stearate was passed through a 500 μm screen and added to the drum blender. The mixture was blended for 5 minutes. The directly-blended final mixture was then encapsulated in a size #1 capsule, 375 mg per capsule (112,000 capsule batch size) using a Dosator type capsule filling machine.

5.5. Example 5

200 mg Thalidomide Dosage Capsule

Table 6 illustrates a batch formulation and single dosage formulation for a 200 mg thalidomide single dose unit, i.e., about 40 percent by weight, in a size #0 capsule.

TABLE 6

Formulation for 200 mg thalidomide capsule

| Material | Percent By Weight | Quantity (mg/capsule) | Quantity (kg/batch) |
|---|---|---|---|
| Thalidomide | 40.0% | 200 mg | 16.80 kg |
| Pregelatinized Corn Starch, NF | 59.5% | 297.5 mg | 24.99 kg |
| Magnesium Stearate | 0.5% | 2.5 mg | 0.21 kg |
| Total | 100.0% | 500 mg | 42.00 kg |

The pregelatinized corn starch (SPRESS B-820) and thalidomide components were passed through a 710 μm screen and then loaded into a Diffusion Mixer with a baffle insert and blended for 15 minutes. The magnesium stearate was passed through a 210 μm screen and added to the Diffusion Mixer. The directly-blended final mixture was then encapsulated in a size #0 capsule, 500 mg per capsule (8400 capsule batch size) using a Dosator type capsule filling machine.

5.6. Example 6

100 mg Thalidomide Dosage Tablet

Table 7 illustrates a batch formulation and a single dose unit formulation for a 100 mg, i.e., 40 percent by weight, thalidomide single dose unit tablet.

TABLE 7

Formulation for 100 mg thalidomide tablet

| Material | Percent by Weight | Quantity (mg/tablet) | Quantity (kg/batch) |
|---|---|---|---|
| Thalidomide | 40% | 100.00 | 20.00 |
| Microcrystalline Cellulose, NF | 53.5% | 133.75 | 26.75 |
| Pluronic F-68 Surfactant | 4.0% | 10.00 | 2.00 |
| Croscarmellose Sodium Type A, NF | 2.0% | 5.00 | 1.00 |
| Magnesium Stearate, NF | 0.5% | 1.25 | 0.25 |
| Total | 100.0% | 250.00 mg | 50.00 kg |

The microcrystalline cellulose, croscarmellose sodium, and thalidomide components were passed through a #30 mesh screen (about 430μ to about 655μ). The Pluronic F-68® (manufactured by JRH Biosciences, Inc. of Lenexa, Kans.) surfactant was passed through a #20 mesh screen (about 457μ to about 1041μ). The Pluronic F-68® surfactant and 0.5 kgs of croscarmellose sodium were loaded into a 16 qt. twin shell tumble blender and mixed for about 5 minutes. The mix was then transferred to a 3 cubic foot twin shell tumble blender where the microcrystalline cellulose was added and blended for about 5 minutes. The thalidomide as added and blended for an additional 25 minutes. This pre-blend was passed through a roller compactor with a hammer mill attached at the discharge of the roller compactor and moved back to the tumble blender. The remaining croscarmellose sodium and magnesium stearate was added to the tumble blender and blended for about 3 minutes. The final mixture was compressed on a rotary tablet press with 250 mg per tablet (200,000 tablet batch size).

5.7. Example 7

Prior Art Thalidomide Dosage Unit

Table 8 illustrates a prior art batch formulation and a single dose unit formulation for a 50 mg, i.e., 12.5 percent by weight, thalidomide single dose unit sized to a capsule of size #0.

TABLE 5

Formulation for 50 mg Thalidomide single dosage unit of size #0

| Material | Percent by Weight | Quantity (mg/capsule) | Quantity (kg/batch) |
|---|---|---|---|
| Thalidomide | 12.5% | 50.0 | 7.50 |
| Microcrystalline Cellulose | 15.0% | 60.0 | 9.00 |
| Kollidon 90F USP[1] | 3.0% | 12.0 | 1.80 |
| Stearic Acid NF | 1.0% | 4.0 | 0.60 |
| Colloidal Silicon Dioxide | 0.2% | 0.8 | 0.12 |
| Crospovidone NF | 4.0% | 16.0 | 2.40 |
| Anhydrous lactose NF | 64.3% | 257.3 | 38.58 |
| Total | 100.0% | 400.0 mg | 60.00 kg |

[1]Also manufactured as Povidone 90F USP by BASF

Microcrystalline cellulose, KOLLIDON 90F, stearic acid, colloidal silicon dioxide, crospovidone, and anhydrous lactose were individually weighed and passed through a 710μ screen. The raw materials were transferred into a bowl or Fielder blender. Subsequently, the quantity of milled thalidomide was weighed and added to the raw materials through the screen, followed by adding the anhydrous lactose. The mixture was blended for about 2.5 minutes to about 6 minutes, until the mixture was homogenous. The blend was compressed by passing the blend through a roller compactor (Alexanderwerk Compactor WP 50 N/75) and milled using a hammer mill. Thereafter, the mixture was encapsulated using a Zanasi AZ20 encapsulating machine (150,000 capsule batch size). The blend mixture was loaded into size #0 hard gelatin capsules to the desired fill weight of powder and 50 mg of thalidomide.

While the invention has been described with respect to the particular embodiments, it will be apparent to those skilled in the art that various changes and modifications may be made without departing from the spirit and scope of the invention as defined in the claims. Such modifications are also intended to fall within the scope of the appended claims.

What is claimed is:

1. A pharmaceutical composition consisting of a uniform admixture of 50 mg thalidomide, pregelatinized corn starch, and 1 mg of magnesium stearate, wherein said composition is suitable for administration to a human in a size 4 capsule and said composition is at least bioequivalent to a thalidomide dosage form which consists of 12.5 percent by weight thalidomide, 15.0 percent by weight microcrystalline cellulose, 3.0 percent by weight povidone having a K-value ranging from 81.0 to 96.3, 1.0 percent by weight stearic acid, 0.2 percent by weight colloidal silicon dioxide, 4.0 percent by weight crospovidone, and 64.3 percent by weight anhydrous lactose.

2. A pharmaceutical composition consisting of a uniform admixture of 100 mg thalidomide, pregelatinized corn starch, and 1.25 mg of magnesium stearate, wherein said composition is suitable for administration to a human in a size 2 capsule and said composition is at least bioequivalent to a thalidomide dosage form which consists of 12.5 percent by weight thalidomide, 15.0 percent by weight microcrystalline cellulose, 3.0 percent by weight povidone having a K-value ranging from 81.0 to 96.3, 1.0 percent by weight stearic acid, 0.2 percent by weight colloidal silicon dioxide, 4.0 percent by weight crospovidone, and 64.3 percent by weight anhydrous lactose.

3. A pharmaceutical composition consisting of a uniform admixture of 150 mg thalidomide, pregelatinized corn starch, and 2 mg of magnesium stearate, wherein said composition is suitable for administration to a human in a size 1 capsule and said composition is at least bioequivalent to a thalidomide dosage form which consists of 12.5 percent by weight thalidomide, 15.0 percent by weight microcrystalline cellulose, 3.0 percent by weight povidone having a K-value ranging from 81.0 to 96.3, 1.0 percent by weight stearic acid, 0.2 percent by weight colloidal silicon dioxide, 4.0 percent by weight crospovidone, and 64.3 percent by weight anhydrous lactose.

4. A pharmaceutical composition consisting of a uniform admixture of 200 mg thalidomide, pregelatinized corn starch, and 2.5 mg of magnesium stearate, wherein said composition is suitable for administration to a human in a size 0 capsule and said composition is at least bioequivalent to a thalidomide dosage form which consists of 12.5 percent by weight thalidomide, 15.0 percent by weight microcrystalline cellulose, 3.0 percent by weight povidone having a K-value ranging from 81.0 to 96.3, 1.0 percent by weight stearic acid, 0.2 percent by weight colloidal silicon dioxide, 4.0 percent by weight crospovidone, and 64.3 percent by weight anhydrous lactose.

5. An oral dosage form in the form of a capsule comprising thalidomide and one or more pharmaceutically acceptable excipients, which oral dosage form is at least bioequivalent to a thalidomide dosage form consisting of 12.5 percent by weight thalidomide, 15.0 percent by weight microcrystalline cellulose, 3.0 percent by weight povidone having a K-value ranging from 81.0 to 96.3, 1.0 percent by weight stearic acid, 0.2 percent by weight colloidal silicon dioxide, 4.0 percent by weight crospovidone, and 64.3 percent by weight anhydrous lactose; wherein the amount of thalidomide is about 40 percent by total weight of the content of the dosage form, and wherein the amount of thalidomide is 50, 100, 150 or 200 mg, and wherein the excipient comprises magnesium stearate in an amount of about 1 percent by total weight of the content in the oral dosage form.

6. The oral dosage form of claim 5, wherein the total weight of the content within the dosage form is about 125 mg and which dosage form is a size 4 capsule.

7. The oral dosage form of claim 5, wherein the total weight of the content within the dosage form is about 250 mg and which dosage form is a size 2 capsule.

8. The oral dosage form of claim 5, wherein the total weight of the content within the dosage form is about 375 mg and which dosage form is a size 1 capsule.

9. The oral dosage form of claim 5, wherein the total weight of the content within the dosage form is about 500 mg and which dosage form is a size 0 capsule.

10. The oral dosage form of claim 5, wherein the excipient comprises pregelatinized starch.

11. The oral dosage form of claim 10, wherein the pregelatinized starch is present at an amount of about 60 percent by total weight of the content in the oral dosage form.

12. The oral dosage form of claim 5, wherein the excipients consists essentially of pregelatinized starch.

* * * * *